US006515167B1

(12) United States Patent
Shieh et al.

(10) Patent No.: US 6,515,167 B1
(45) Date of Patent: Feb. 4, 2003

(54) LOW TEMPERATURE PROCESS FOR PREPARING METHYL ESTERS

(75) Inventors: Wen-Chung Shieh, Berkeley Heights, NJ (US); Steven J. Dell, Madison, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/134,347

(22) Filed: Apr. 26, 2002

Related U.S. Application Data

(63) Continuation-in-part of application No. 09/981,941, filed on Oct. 17, 2001, now abandoned.

(51) Int. Cl.$^7$ ..................... C07C 69/02; C07C 229/00
(52) U.S. Cl. ................ 560/231; 560/8; 560/9; 560/147; 560/155; 560/205; 558/260
(58) Field of Search ................ 560/231, 8, 9, 560/147, 155, 179, 205; 558/260

(56) References Cited

U.S. PATENT DOCUMENTS

| | | | |
|---|---|---|---|
| 4,513,146 A | * | 4/1985 | Thompson |
| 5,387,718 A | | 2/1995 | Köhler et al. ............... 568/38 |
| 5,453,516 A | | 9/1995 | Fischer et al. ............. 548/543 |

OTHER PUBLICATIONS

Shieh et al, Journal of Organic Chemistry, (Apr. 5, 2002), vol. 67, No. 7, pp. 2188–2191.*
*Wang et al., "A Novel Route to Pyrrolo[2–1–c][1,4] benzodiazepin–5–ones. Formal Total Synthesis of (±)–DC–81.", Org. Lett., vol. 1, No. 11, pp. 1835–1837 (1999).
*Chakraborti et al., "Chemoselective Protection of Carboxylic Acid as Methyl Ester: A Practical Alternative to Diazomethane Protocol", J. Org. Chem., vol. 64, No. 21, pp. 8014–8017 (1999).
*Selva et al., "Selective Mono–N–Methylation of Primary Aromatic Amines by Dimethyl Carbonate over Faujasite X–and Y–type Zeolites", J. Chem. Soc., Perkin Trans., vol. 1, pp. 1041–1045 (1997).
*Selva et al., "Reaction of Primary Aromatic Amines with Alkyl Carbonates over NaY Faujasite: A Convenient and Selective Access to Mono–N–alkyl Anilines", J. Org. Chem., vol. 66, No. 3, pp. 677–680 (2001).
*Bomben et al., "A New Synthesis of 2–Aryloxypropionic Acids Derivatives via Selective Mono–C–Methylation of Methyl Aryloxyacetates and Aryloxyacetonitriles with Dimethyl Carbonate", Tetrahedron, vol. 51, No. 42, pp. 11573–11580 (1995).
*Aggarwal et al., "Superior Amine Catalysts for the Baylis–Hillman Reaction: the Use of DBU and Its Implications", Chem. Commun., pp. 2311–2312 (1999).
*Perosa et al., "Alkyl Methyl Carbonates as Methylating Agents. The O–Methylation of Phenols.", Synlett, Nos. 1–2, pp. 272–274 (2000).
*Selva et al., "Selective Mono–methylation of Arylacetonitriles and Methyl Arylacetrates by Dimethyl Carbonate", J. Chem. Soc. Perkin Trans. 1, pp. 1323–1328 (1994).
*Tundo et al., "Selective and Continuous–flow Mono–methylation of Arylacetonitriles with Dimethyl Carbonate under Gas–Liquid Phase–Transfer Catalysis Conditions", J. Chem. Soc. Perkin Trans. 1, pp. 1070–1071 (1989).
*Tundo, P., "Selective monomethylation reactions of methylene–active compounds with dimethylcarbonate. An example of clean synthesis", Pure Appl. Chem., vol. 72, No. 9, pp. 1793–1797 (2000).

(List continued on next page.)

*Primary Examiner*—Paul J. Killos
*Assistant Examiner*—Héctor M Reyes
(74) *Attorney, Agent, or Firm*—John D. Thallemer

(57) ABSTRACT

A low temperature process for preparing a methyl ester having formula (III)

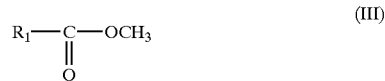

said process comprising reacting a carboxylic acid or salt thereof having formula (I)

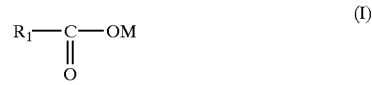

with dimethyl carbonate having formula (II)

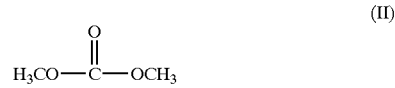

in the presence of a catalyst selected from the group consisting of 1,8 diazabicyclo[5.4.0]undec-7-ene; 1,4-diazabicyclo[2.2.2]octane; and combinations thereof, wherein said process is conducted at a temperature of about 10° C. to less than 120° C.;

$R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl and haloalkyl; and M is selected from the group consisting of hydrogen, a monovalent metal and a monovalent fractional part of a polyvalent metal. The process is especially advantageous for preparing methyl esters since the process: (1) is conducted at a low temperature, less than 120 ° C.; (2) utilizes an environmentally friendly methylating reagent, dimethylcarbonate; (3) produces a high yield of the methyl ester, generally 97–98% conversion; and (4) does not require a high-pressure (autoclave) reactor.

17 Claims, No Drawings

OTHER PUBLICATIONS

Campbell et al., Microwave Accelerated Preparation of Aryl 2-(N,N-diethylamino)ethyl Ethers, 1994, Bioorganic and Medicinal Chemistry Letters, 4(21) pp. 2627-2630.

Basak et al., "Chemoselective O-Methylation of Phenols under Non-aqueous Condition", Ttrahedron Lett., vol. 39, pp. 4883-4886 (1998).

Voskresensky et al., "Selective One-Pot N-Monomethylation of 2-Nitroanilines under PTC Conditions", Syn. Comm., vol. 30, No. 19, pp. 3523-3526 (2000).

Lissel et al., "Dimethylcarbonat als Methylierungsmittel unter Phasen-Transfer-Katalytischen Bedingungen", Synthesis, vol. 5, pp. 382-383 (1986).

Barcelo et al., "Penaalkylguanidines as Etherification and Esterification Catalysts", Tetrahedron, vol. 46, No. 6, pp. 1839-1848 (1990).

Lee et al., "Convenient O-Methylation of Phenols with Dimethyl Carbonate", SynLett, pp. 1063-1064 (1998).

Ahmad et al., "Preparation of 3-Substituted 6,7-Dimethoxyquinoxalin-2(1H) ones and Studies of Their Potential as Fluroionophores", Tetrahedron, vol. 51, No. 47, pp. 12899-12910 (1995).

Johnstone et al., "A Rapid, Simple and Mild Procedure for Alkylation of Phenols, Alcohols, Amides and Acids", Tetrahedron, vol. 35, pp. 2169-2173 (1979).

Granitrza et al., "Efficiant Acylation of Hydroxy Functions by Means of Fmoc Amino Acie Fluorides".

"CRC Handbook of Chemistry andPhysics", (D.R.Lind, Ed.), 75$^{th}$ Edition,CRC Press, Inc., pp. 8-45-8-55 (1994).

Kanie et al., "A Facile Synthesis of Trifluoromethylamines by Oxidative Desulfurization-Fluorination of Dithicarbamates", bull. Chem. Soc. Jpn., vol. 71, No. 8, pp. 1973-1991 (1998).

* cited by examiner

LOW TEMPERATURE PROCESS FOR PREPARING METHYL ESTERS

FIELD OF THE INVENTION

The present invention provides a process for preparing a methyl ester by reacting a carboxylic acid or salt thereof with dimethyl carbonate in the presence of a catalyst selected from 1,8-diazabicyclo[5.4.0]undec-7-ene (DBU), and 1,4-diazabicyclo[2.2.2]octane (DABCO).

BACKGROUND OF THE INVENTION

Methylation of alcohols, amines, carboxylic acids and activated methylenes is an important process in chemistry. However, due to the environmental and human impact of using toxic and unsafe methylating reagents, such as methyl iodide or dimethyl sulfate, the investigation of safer, generally applicable alternatives continues. As an alternative to these toxic methylating agents, dimethyl carbonate has attracted considerable attention for the methylation of phenols, anilines and activated methylenes. Dimethyl carbonate is non-toxic and generates $CO_2$ and methanol as by-products during methylations. Dimethyl carbonate is also a volatile liquid with a boiling point of 90° C. Hence, the unreacted dimethyl carbonate can be easily recovered by distillation from the reaction mixture and reused. Furthermore, dimethyl carbonate has been shown to be quite selective in monomethylation of primary aromatic amines and C-methylation of arylacetonitriles and arylacetoesters.

However, the use of dimethyl carbonate as a methylating regent requires high temperatures and pressures, generally 140° C.–180° C. Therefore, autoclaves or the use of asymmetrical carbonates with a higher boiling point than dimethyl carbonate have to be employed. These restrictions lower the popularity of using dimethyl carbonate as a methylating reagent.

U.S. Pat. No. 4,513,146 describes a method for producing esters from highly-hindered carboxylic acids and carbonates. The method involves reacting the highly-hindered carboxylic acid with a carbonate with or without a catalyst at a temperature of 175° C. according to the examples. U.S. Pat. No. 4,513,146 states that exemplary catalysts are nitrogen-containing heterocyclic catalysts such as pyridine, 4-(dimethylamino)pyridine, imidazole, 2,6-lutidine and 2,4,6-collidine.

Therefore, it would be advantageous from a production and safety standpoint to develop a low temperature process which utilizes dimethyl carbonate as a reactant in the production of esters.

SUMMARY OF THE INVENTION

The invention provides a low temperature process for preparing a methyl ester having formula (III)

said process comprising reacting a carboxylic acid or salt thereof having formula (I)

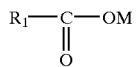

with dimethyl carbonate having formula (II)

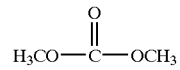

in the presence of a catalyst selected from the group consisting of 1,8-diazabicyclo[5.4.0]undec-7-ene; 1,4-diazabicyclo[2.2.2]octane; and combinations thereof, wherein said process is conducted at a temperature of about 10° C. to less than 120° C.;

$R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl and haloalkyl; and M is selected from the group consisting of hydrogen, a monovalent metal and a monovalent fractional part of a polyvalent metal.

According to another aspect, the invention provides a compound having formula (III)

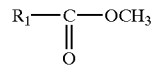

wherein said compound is prepared by a process comprising reacting a carboxylic acid or salt thereof having formula (I)

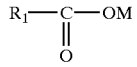

with dimethyl carbonate having formula (II)

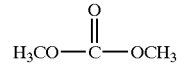

in the presence of a catalyst selected from the group consisting of 1,8-diazabicyclo[5.4.0]undec-7-ene; 1,4-diazabicyclo[2.2.2]octane; and combinations thereof, wherein said process is conducted at a temperature of about 10° C. to less than 120° C.;

$R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl and haloalkyl; and M is selected from the group consisting of hydrogen, a monovalent metal and a monovalent fractional part of a polyvalent metal.

The process of the invention is especially advantageous for preparing methyl esters since the process: (1) is conducted at a low temperature, less than 120° C.; (2) utilizes an environmentally friendly methylating reagent, dimethylcarbonate; (3) produces a high yield of the methyl ester, generally 97–98% conversion; and (4) does not require a high-pressure (autoclave) reactor.

DESCRIPTION OF THE INVENTION

The process of the invention is used to prepare a methyl ester having formula (III)

(III)

In formula (III), $R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl and haloalkyl. The reaction is conducted in the presence of a catalyst which is selected from 1,8-diazabicyclo[5.4.0]undec-7-ene (DBU) and 1,4-diazabicyclo[2.2.2]octane (DABCO). A combination of catalysts may also be used.

The process of the invention involves reacting a carboxylic acid or salt thereof having formula (I)

(I)

with dimethyl carbonate having formula (II)

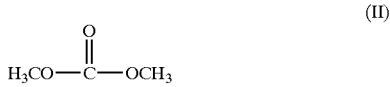
(II)

In formula (I), $R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl and haloalkyl, and M is selected from the group consisting of hydrogen, a monovalent metal and a monovalent fractional part of a polyvalent metal. The metal is preferably selected from sodium, potassium, magnesium or calcium.

As used herein, "alkyl" means straight chain or branched alkyl, which may be, for example, $C_1$–$C_{10}$-alkyl, such as methyl, ethyl, n-propyl, isopropyl, n-butyl, isobutyl, sec-butyl, tert-butyl, straight or branched pentyl, straight or branched hexyl, straight or branched heptyl, straight or branched nonyl or straight or branched decyl. Preferably alkyl is $C_1$–$C_4$-alkyl. "Aryl" means $C_6$–$C_{14}$-aryl, preferably $C_6$–$C_{10}$-aryl, and may be, for example, substituted by at least one group selected from mercapto, dialkylamino, nitro, alkoxy, halogen, keto, cyano or a combination. Preferably aryl is phenyl.

"Alkoxy" means straight chain or branched alkoxy and may be, for example, $C_1$–$C_{10}$-alkoxy, such as methoxy, ethoxy, n-propoxy, isopropoxy, n-butoxy, isobutoxy, sec-butoxy, tert-butoxy or straight or branched pentoxy, hexyloxy, heptyloxy, octyloxy, nonyloxy or decyloxy. Preferably alkoxy is $C_1$–$C_4$-alkoxy.

"Alkenyl" means straight chain or branched alkenyl, which may be, for example, $C_2$–$C_{10}$ alkenyl, such as vinyl, 1-propenyl, 2-propenyl, 1-butenyl, isobutenyl, or straight or branched pentenyl, hexenyl, heptenyl, octenyl, nonenyl or decenyl. Preferred alkenyl is $C_2$–$C_4$-alkenyl.

"Cycloalkyl" means $C_3$–$C_{10}$-cycloalkyl having 3- to 8-ring carbon atoms and may be, for example, cyclopropyl, cyclobutyl, cyclopentyl, cyclohexyl, cycloheptyl or cycloheptyl, any of which can be substituted by one, two or more $C_1$–$C_4$-alkyl groups, particularly methyl groups. Preferably, cycloalkyl is $C_3$–$C_6$-cycloalkyl.

"Benzocycloalkyl" means cycloalkyl (e.g., one of the $C_3$–$C_{10}$-cycloalkyl groups mentioned hereinbefore), attached at two adjacent carbon atoms to a benzene ring. Preferably, benzocycloalkyl is benzo-$C_5$–$C_6$-cycloalkyl, especially benzocyclohexyl (tetrahydronaphthyl).

"Cycloalkylalkyl" means $C_3$–$C_{10}$-cycloalkyl-$C_1$–$C_{10}$-alkyl, where the $C_3$–$C_{10}$-cycloalkyl group has 3- to 8-ring carbon atoms and may be, for example, one of the $C_1$–$C_{10}$-alkyl groups mentioned hereinbefore, particularly one of the $C_1$–$C_4$-alkyl groups, substituted by one of the $C_3$–$C_{10}$-cycloalkyl groups mentioned hereinbefore. Preferably cycloalkylalkyl is $C_3$–$C_6$-cycloalkyl-$C_1$–$C_4$-alkyl.

"Aralkyl" means straight chain or branched $C_6$–$C_{10}$-aryl-$C_1$–$C_{10}$-alkyl and may be, for example, one of the $C_1$–$C_{10}$-alkyl groups mentioned hereinbefore, particularly one of the $C_1$–$C_4$-alkyl groups, substituted by phenyl, tolyl, xylyl or naphthyl. Preferably, aralkyl is phenyl-$C_1$–$C_4$-alkyl, particularly benzyl or 2-phenylethyl.

"Heterocyclic" means a monovalent heterocyclic group having up to 20 carbon atoms and one, two, three or four heteroatoms selected from nitrogen, oxygen and sulfur, the group optionally having an alkyl, alkylcarbonyl, hydroxyalkyl, alkoxyalkyl or aralkyl group attached to a ring carbon or nitrogen atom and being linked to the remainder of the molecule through a ring carbon atom, and may be, for example, a group, preferably a monocyclic group, with one nitrogen, oxygen or sulfur atom such as pyrryl, pyridyl, piperidyl, furyl, tetrahydrofuryl or thienyl, or a group, preferably a monocyclic group, with two hetero atoms selected from nitrogen, oxygen and sulfur, such as imidazolyl, pyrimidinyl, piperazinyl, oxazolyl, isoxazolyl, thiazolyl, morpholinyl or thiomorpholinyl. Preferably, heterocyclic is a monocyclic group having 5- or 6-ring atoms and one or two nitrogen atoms, or one nitrogen atom and one oxygen atom, in the ring and optionally substituted on a ring nitrogen atom by $C_1$–$C_4$-alkyl, hydroxy-$C_1$–$C_4$-alkyl, $C_1$–$C_4$-alkylcarbonyl or phenyl-$C_1$–$C_4$-alkyl.

"Heteroaralkyl" means straight chain or branched aralkyl (e.g., one of the $C_6$–$C_{10}$-aryl-$C_1$–$C_{10}$-alkyl groups mentioned hereinbefore) substituted by one or more heterocyclic groups.

"Alkoxyalkyl" means straight chain or branched alkyl substituted by one or more alkoxy groups and may be, for example, a $C_1$–$C_{10}$-alkoxy-$C_1$–$C_{10}$-alkyl group, such as one of the $C_1$–$C_{10}$-alkyl groups, particularly one of the $C_1$–$C_4$-alkyl groups, mentioned hereinbefore substituted by one of the $C_1$–$C_{10}$-alkoxy groups, preferably one of the $C_1$–$C_4$-alkoxy groups mentioned hereinbefore. Preferably alkoxyalkyl is $C_1$–$C_4$-alkoxy-$C_1$–$C_4$-alkyl.

"Carboxyalkyl" means straight chain or branched alkyl, for example, $C_1$–$C_{10}$-alkyl, such as one of the $C_1$–$C_{10}$-alkyl groups mentioned hereinbefore, substituted, preferably on a primary carbon atom, by a carboxyl group. Preferably carboxyalkyl is carboxy-$C_1$–$C_4$-alkyl.

"Alkylcarbonyl" means a group $R_2C=O$ wherein $R_2$ is alkyl, for example, $C_1$–$C_{10}$-alkyl, such as one of the $C_1$–$C_{10}$-, preferably $C_1$–$C_4$-, alkyl groups mentioned hereinbefore. Preferably, alkylcarbonyl is $C_1$–$C_4$-alkylcarbonyl, for example, $R_2C=O$ wherein $R_2$ is $C_1$–$C_4$-alkyl.

"Alkoxycarbonyl" means a group $R_3CO$ wherein $R_3$ is an alkoxy group, for example, a $C_1$–$C_{10}$-alkoxy group, such as one of the $C_1$–$C_{10}$, preferably $C_1$–$C_4$, alkoxy groups mentioned hereinbefore. Preferably, alkoxycarbonyl is $C_1$–$C_4$-alkoxycarbonyl, for example, $R_3CO$, wherein $R_3$ is $C_1$–$C_4$-alkoxy.

"Alkoxycarbonylalkyl" means straight or branched chain alkyl, for example, a $C_1$–$C_{10}$-alkyl group, such as one of the $C_1$–$C_{10}$-, preferably $C_1$–$C_4$-, alkyl groups mentioned hereinbefore, substituted by an alkoxycarbonyl group as hereinbefore defined. Preferably, alkoxycarbonylalkyl is $C_1$–$C_4$-alkoxy-carbonyl-$C_1$–$C_4$-alkyl.

"Haloalkyl" means straight chain or branched alkyl, for example, $C_1$–$C_{10}$-alkyl, such as one of the $C_1$–$C_{10}$-alkyl groups mentioned hereinbefore, substituted by one or more, for example, one, two or three halogen atoms, preferably fluorine or chlorine atoms. Preferably haloalkyl is $C_1$–$C_4$-alkyl substituted by one, two or three fluorine or chlorine atoms.

Specific examples of carboxylic acids of formula (I) are 2,6-dimethoxybenzoic acid, 2,3:4,6-di-O-isopropylidene-α-L-xylo-2-hexulofuranosonate monohydrate, N-α-t-boc-L-proline, benzoic acid, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, 2,2-dimethylpropanoic acid, 2,2-dimethylbutanoic acid, 2,2-dimethyloctanoic acid and the sodium and potassium salts thereof. A combination of carboxylic acids may also be used. Preferably the carboxylic acid is selected from 2,6-dimethoxybenzoic acid, 2,3:4,6-di-O-isopropylidene-α-L-xylo-2-hexulofuranosonate monohydrate, N-α-t-boc-L-proline, and benzoic acid.

The process of the invention is preferably conducted in the liquid phase. It may be carried out batchwise, continuously, semi-batchwise or semi-continuously. When the dimethyl carbonate is a liquid under the conditions of the reaction, it may act as a solvent for the carboxylic acid or salt thereof. Typically, but not necessarily, excess dimethyl carbonate is employed relative to the amount of carboxylic acid or salt thereof, and this usually serves to dissolve the carboxylic acid or salt thereof throughout the reaction. In many cases, one or more by-products of the reaction, most notably methanol, also tend to dissolve the carboxylic acid or salt thereof. Although extrinsic solvent is not ordinarily employed, it may be used when desired or when necessary to dissolve one or more of the reactants. Examples of suitable extrinsic solvents include: acetonitrile, ethyl acetate, acetone, benzene, toluene, dioxane, dimethylformamide and chlorinated solvents, such as chloroform, methylene chloride, ethylene chloride, carbon tetrachloride and chlorobenzene. A combination of solvents may also be used. Preferably, the process is conducted without an extrinsic solvent.

The process of the invention is conducted at a temperature of from about 10° C. to less than 120° C., preferably, 70° C.–100° C.; and more preferably from about 90° C. to less than 100° C. The process is conducted preferably under a pressure of from about 1 atm to about 100 atm, more preferably, from 1 atm to 50 atm. Most preferably, the process is conducted under a pressure of 1 atm.

The equivalent ratio of the catalyst to the carboxylic acid or salt thereof initially present may vary widely, but preferably is in the range of from about 0.01:1 to about 2:1. More preferably, the equivalent ratio of the catalyst to the carboxylic acid or salt thereof initially present is from about 0.1:1 to about 1:1, most preferably, about 1:1.

In one embodiment of the invention, an amine base is used in the process of the invention to prepare a methyl ester. Preferred amine bases are trialkylamines and ethylenediamines. Specific amine bases include, but are not limited to, triethylamine, N,N-diisopropylethylamine and N,N'-diisopropylethylenediamine. A combination of amine bases may also be used.

Following preparation, the methyl ester may be recovered from the reaction mixture by any of the various techniques known to the art. Distillation at reduced pressure is a preferred technique.

The following non-limiting examples illustrate further aspects of the invention.

EXAMPLE 1

Preparation of methyl 2,6-dimethoxybenzoate using DBU catalyst

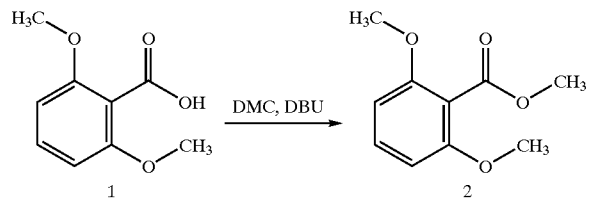

1,8-diazabicyclo[5.4.0]undec-7-ene (DBU), (836 mg, 5.49 mmol), was added to a mixture of 2,6-dimethoxybenzoic acid (1), (1.0 g, 5.49 mmol), in dimethyl carbonate (DMC) (10 mL) and the resulting mixture was heated to reflux at 90° C. for 4 hours. The reaction mixture was cooled to 25° C. and diluted with EtOAc (30 mL) and water (30 mL). The organic layer was separated and washed in sequence with 10 mL of water, 2 M HCl (2×30 mL), saturated aqueous $NaHCO_3$ (2×30 mL) and water (2×25 mL). The organic layer was dried over $Na_2SO_4$, filtered and concentrated under vacuum to give methyl 2,6-dimethoxybenzoate (2) as a white solid. The yield of the 2,6-dimethoxybenzoate as determined by HPLC was 97–98% conversion.

EXAMPLE 2

Preparation of methyl 2,3:4,6-di-O-isopropylidene-α-L-xylo-2-hexulofuranosonate using DBU catalyst

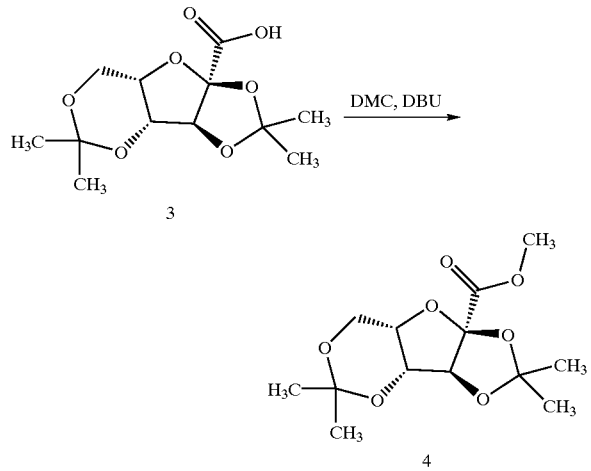

To a solution of 2,3:4,6-di-O-isopropylidene-α-L-xylo-2-hexulofuranosonate monohydrate (3), (1.0 g, 3.42 mmol), in DMC (10 mL), DBU (521 mg, 3.42 mmol) was added and the resulting solution was heated to reflux (90° C.) for 16 hours. The reaction mixture was cooled to ambient temperature and diluted with $CH_2Cl_2$ (40 mL) and water (40 mL). The organic layer was separated and washed in sequence with water (40 mL), 10% aqueous citric acid (2×40 mL), saturated aqueous NaHCO$_3$ (40 mL) and water (2×40 mL). The organic layer was dried over Na$_2$SO$_4$, filtered and concentrated under vacuum to give the crude product, which was purified using silica gel chromatography (7:3 hexane/EtOAc) to afford methyl 2,3:4,6-di-O-isopropylidene-α-L-xylo-2-hexulofuranosonate (4) as an oil. The yield of the methyl 2,3:4,6-di-O-isopropylidene-α-L-xylo-2-hexulofuranosonate as determined by HPLC was 97–98% conversion.

EXAMPLE 3

Preparation of N-α-t-boc-L-proline methyl ester using DBU catalyst

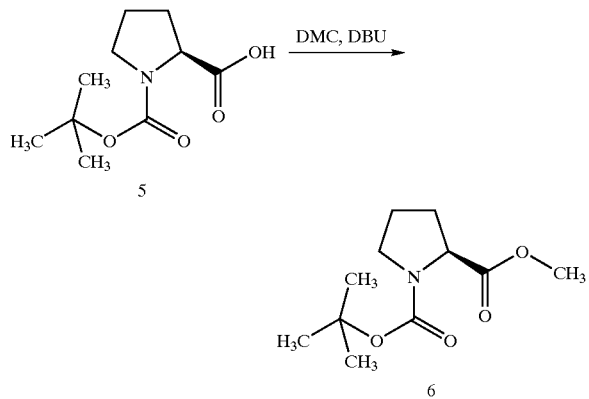

To a mixture of N-α-t-boc-L-proline (5) (1.0 g, 4.65 mmol) in DMC (10 mL), DBU (708 mg, 4.65 mmol) was added and the resulting solution was heated to reflux (90° C.) for 19.5 hours. The reaction mixture was cooled to ambient temperature and diluted with EtOAc (40 mL) and water (40 mL). The organic layer was separated and washed in sequence with 10% aqueous citric acid (2×40 mL), saturated aqueous NaHCO$_3$ (40 mL), and water (2×40 mL). The organic layer was dried over Na$_2$SO$_4$, filtered and concentrated under vacuum to give N-α-t-boc-L-proline methyl ester (6) as an oil. The yield of the N-α-t-boc-L-proline methyl ester as determined by HPLC was 97–98% conversion.

EXAMPLE 4

Preparation of methyl benzoate using DABCO catalyst

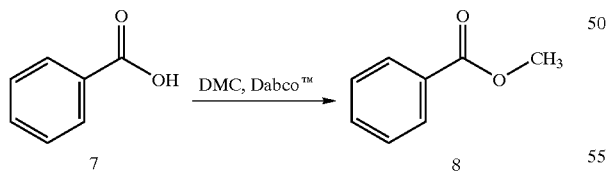

Dabco™ (1.84 g, 16.4 mmol), commercially available from Aldrich, was added to a mixture of benzoic acid (7) (2.0 g, 16.4 mmol) in DMC (20 mL) and the resulting mixture was heated to reflux (90° C.) for 7.5 hours. The reaction mixture was cooled to ambient temperature and diluted with CH$_2$Cl$_2$ (50 mL) and water (40 mL). The organic layer was separated and washed in sequence with 2 M HCl (2×40 mL), saturated aqueous NaHCO$_3$ (40 mL) and water (2×40 mL). The organic layer was dried over Na$_2$SO$_4$, filtered and concentrated under vacuum to give methyl benzoate (8) as an oil. The yield of the methyl benzoate as determined by HPLC was 97–98% conversion.

EXAMPLE 5

Preparation of methyl benzoate using DBU catalyst

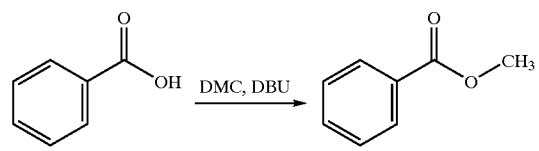

DBU (2.5 g, 16.4 mmol) was added to a mixture of benzoic acid (2.0 g, 16.4 mmol) in DMC (20 mL) and the resulting mixture was heated to reflux (90° C.) for 2.5 hours. The reaction mixture was cooled to ambient temperature and diluted with CH$_2$Cl$_2$ (50 mL) and water (40 mL). The organic layer was separated and washed in sequence with 2 M HCl (2×40 mL), saturated aqueous NaHCO$_3$ (40 mL) and water (2×40 mL). The organic layer was dried over Na$_2$SO$_4$, filtered and concentrated under vacuum to give methyl benzoate as an oil. The yield of the methyl benzoate as determined by HPLC was 97–98% conversion.

EXAMPLE 6

(Comparative)

Preparation of methyl benzoate using ammonium benzoate as a base without a catalyst

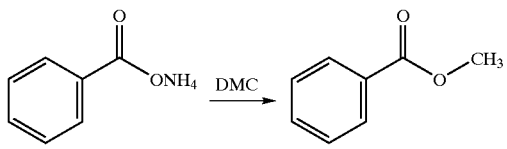

A mixture of ammonium benzoate (1 g, 8.2 mmol), DMC (10 mL) and dimethylformamide (DMF) (3 mL) was heated to reflux (90° C.) for 24 hours. HPLC indicated less than 1% of methyl benzoate.

EXAMPLE 7

(Comparative)

Preparation of methyl benzoate using tributylamine as a base without a catalyst

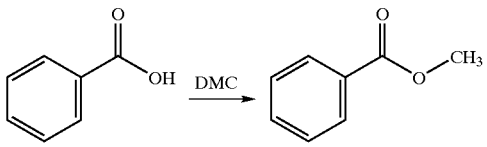

Tributylamine (1.5 g, 0.2 mmol) was added to a mixture of benzoic acid (1.0 g, 0.2 mmol) in DMC (10 mL) and the resulting mixture was heated to reflux (90° C.) for 48 hours. HPLC indicated less than 1 % of methyl benzoate.

EXAMPLE 8

Preparation of methyl phenylacetate

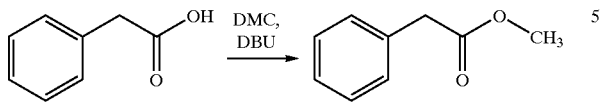

DBU (3.35 g, 22.0 mmol) was added to a mixture of phenylacetic acid (3.0 g, 22.0 mmol) in DMC (30 mL) and the resulting mixture was heated to reflux (90° C.) for 24 hours. The reaction mixture was cooled to ambient temperature and diluted with $CH_2Cl_2$ (50 mL) and water (40 mL). The organic layer was separated and washed in sequence with 2 M HCl (2×40 mL), saturated aqueous $NaHCO_3$ (40 mL) and water (2×40 mL). The organic layer was dried over $Na_2SO_4$, filtered and concentrated under vacuum to give methyl phenylacetate as an oil.

EXAMPLE 9

Preparation of methyl 2-phenylpropionate

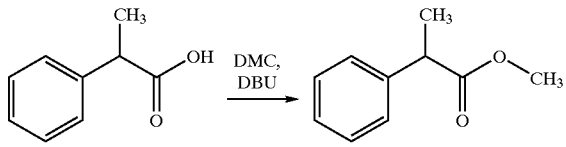

DBU (2.03 g, 13.3 mmol) was added to a mixture of 2-phenylpropionic acid (2.0 g, 13.3 mmol) in DMC (20 mL) and the resulting mixture was heated to reflux (90° C.) for 5 hours. The reaction mixture was cooled to ambient temperature and diluted with $CH_2Cl_2$ (50 mL) and water (40 mL). The organic layer was separated and washed in sequence with 2 M HCl (2×40 mL), saturated aqueous $NaHCO_3$ (40 mL) and water (2×50 mL). The organic layer was dried over $Na_2SO_4$, filtered and concentrated under vacuum to give methyl 2-phenylpropionate as an oil.

The process of the invention is especially advantageous for preparing methyl esters since the process: (1) is conducted at a low temperature, less than 120° C.; (2) utilizes an environmentally friendly methylating reagent, dimethylcarbonate; (3) produces a high yield of the methyl ester, generally 97–98% conversion; and (4) does not require a high-pressure (autoclave) reactor.

While the invention has been described with particular reference to certain embodiments thereof, it will be understood that changes and modifications may be made by those of ordinary skill within the scope and spirit of the following claims:

What is claimed is:

1. A low temperature process for preparing a methyl ester having formula (III)

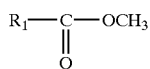 (III)

said process comprising reacting a carboxylic acid or salt thereof having formula (I)

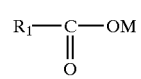 (I)

with dimethyl carbonate having formula (II)

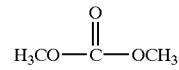 (II)

in the presence of a catalyst selected from the group consisting of 1,8-diazabicyclo[5.4.0]undec-7-ene; 1,4-diazabicyclo[2.2.2]octane; and combinations thereof, wherein said process is conducted at a temperature of about 10° C. to less than 120° C.;

$R_1$ is selected from the group consisting of an alkyl, aryl, alkoxy, alkenyl, cycloalkyl, benzocycloalkyl, cycloalkylalkyl, aralkyl, heterocyclic, heteroaralkyl, alkoxyalkyl, carboxyalkyl, alkylcarbonyl, alkoxycarbonyl, alkoxycarbonylalkyl and haloalkyl; and M is selected from the group consisting of hydrogen, a monovalent metal and a monovalent fractional part of a polyvalent metal.

2. The process according to claim 1, wherein M is selected from the group consisting of hydrogen, sodium, potassium, magnesium and calcium.

3. The process according to claim 2, wherein M is hydrogen.

4. The process according to claim 1, wherein $R_1$ is substituted by at least one group which is selected from the group consisting of mercapto, dialkylamino, nitro, alkoxy, halogen, keto, cyano and combinations thereof.

5. The process according to claim 4, wherein $R_1$ is substituted by at least one group which is selected from the group consisting of dialkylamino, alkoxy, and halogen.

6. The process according to claim 1, wherein the carboxylic acid is selected from the group consisting of 2,6-dimethoxybenzoic acid, 2,3:4,6-di-O-isopropylidene-α-L-xylo-2-hexulofuranosonate monohydrate, N-α-t-boc-L-proline, benzoic acid, phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, 2,2-dimethylpropanoic acid, 2,2-dimethylbutanoic acid, 2,2-dimethyloctanoic acid and the sodium and potassium salts thereof.

7. The process according to claim 6, wherein the carboxylic acid is selected from the group consisting of 2,6-dimethoxybenzoic acid, 2,3:4,6-di-O-isopropylidene-α-L-xylo-2-hexulofuranosonate monohydrate, N-α-t-boc-L-proline and benzoic acid.

8. The process according to claim 1, which is conducted in the presence of an extrinsic solvent.

9. The process according to claim 8, wherein the extrinsic solvent is selected from the group consisting of acetonitrile, ethyl acetate, acetone, benzene, toluene, dioxane, dimethylformamide, chloroform, methylene chloride, ethylene chloride, carbon tetrachloride, chlorobenzene and combinations thereof.

10. The process according to claim 9, wherein the extrinsic solvent is ethyl acetate or acetone.

11. The process according to claim 1, wherein the temperature is from about 70° C. to about 100° C.

12. The process according to claim 11, wherein the temperature is from about 90° C. to less than 100° C.

13. The process according to claim 1, wherein the equivalent ratio of the catalyst to the carboxylic acid or salt thereof initially present is from 0.01:1 to 2:1.

14. The process according to claim 13, wherein the equivalent ratio of the catalyst to the carboxylic acid or salt thereof initially present is from 0.1:1 to 1:1.

15. The process according to claim 1, wherein the methyl ester is recovered from the process by distillation at reduced pressure.

16. The process according to claim 1, which further comprises an amine base.

17. The process according to claim 16, wherein the amine base is selected from the group consisting of triethylamine, N,N-diisopropylethylamine and N,N'-diisopropylethylenediamine.

* * * * *